US010718838B2

(12) United States Patent
Koch et al.

(10) Patent No.: US 10,718,838 B2
(45) Date of Patent: Jul. 21, 2020

(54) SYSTEMS AND METHODS FOR CALIBRATED MULTI-SPECTRAL MAGNETIC RESONANCE IMAGING

(71) Applicant: THE MEDICAL COLLEGE OF WISCONSIN, INC., Milwaukee, WI (US)

(72) Inventors: Kevin M. Koch, Wauwatosa, WI (US); Suryanarayanan Sivaram Kaushik, Milwaukee, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 8 days.

(21) Appl. No.: 15/573,945

(22) PCT Filed: May 13, 2016

(86) PCT No.: PCT/US2016/032383
§ 371 (c)(1),
(2) Date: Nov. 14, 2017

(87) PCT Pub. No.: WO2016/187014
PCT Pub. Date: Nov. 24, 2016

(65) Prior Publication Data
US 2018/0292491 A1 Oct. 11, 2018

Related U.S. Application Data

(60) Provisional application No. 62/162,001, filed on May 15, 2015.

(51) Int. Cl.
*G01R 33/54* (2006.01)
*G01R 33/24* (2006.01)
(Continued)

(52) U.S. Cl.
CPC .......... *G01R 33/543* (2013.01); *A61B 5/0037* (2013.01); *A61B 5/055* (2013.01);
(Continued)

(58) Field of Classification Search
CPC ................ G01R 33/543; G01R 33/583; G01R 33/56563; G01R 33/56536; G01R 33/243; G01V 3/14
See application file for complete search history.

(56) References Cited

U.S. PATENT DOCUMENTS 7,928,729 B2    4/2011   Hargreaves et al.
8,482,279 B2    7/2013   Chen et al.
(Continued)

FOREIGN PATENT DOCUMENTS

WO    2014/071249 A1    5/2014

OTHER PUBLICATIONS

International Search Report and Written Opinion for International Patent Application No. PCT/US2016/032383 dated Aug. 16, 2016.

*Primary Examiner* — Dominic E Hawkins
(74) *Attorney, Agent, or Firm* — Quarles & Brady LLP

(57) ABSTRACT

Systems and methods are provided for performing a calibration "pre-scan" prior to acquiring data using a magnetic resonance imaging ("MRI") system performing a multi-spectral imaging ("MSI") acquisition. Information from the calibration scan is used to optimize the scanning and data collection during the MSI scan. As a result, scan times and motion artifacts are reduced. In addition, image resolution can also be increased, thereby improving image quality. As one example, the MSI acquisition can be a MAVRIC acquisition. In general, the calibration data is used to determine the minimum number of spectral bins required to achieve acceptable image quality near a specific metallic implant or device.

29 Claims, 4 Drawing Sheets

(51) Int. Cl.
   *G01R 33/565* (2006.01)
   *A61B 5/055* (2006.01)
   *A61B 5/00* (2006.01)
   *G01V 13/00* (2006.01)
   *G01V 3/14* (2006.01)
   *G01R 33/58* (2006.01)

(52) U.S. Cl.
   CPC ..... *G01R 33/243* (2013.01); *G01R 33/56536* (2013.01); *G01R 33/56563* (2013.01); *G01R 33/583* (2013.01); *G01V 3/14* (2013.01); *G01V 13/00* (2013.01)

(56) References Cited

U.S. PATENT DOCUMENTS

| | | | |
|---|---|---|---|
| 8,995,738 B2 | 3/2015 | Hernando et al. | |
| 10,061,007 B2* | 8/2018 | Gui | G01R 33/56536 |
| 2006/0091881 A1* | 5/2006 | Clarke | G01R 33/326 |
| | | | 324/301 |
| 2007/0091428 A1* | 4/2007 | Wilson | G02B 21/365 |
| | | | 359/391 |
| 2007/0241753 A1 | 10/2007 | Sodickson et al. | |
| 2011/0103670 A1* | 5/2011 | Koch | G01R 33/243 |
| | | | 382/131 |
| 2011/0241669 A1* | 10/2011 | Chen | G01R 33/5611 |
| | | | 324/309 |
| 2011/0262017 A1 | 10/2011 | Haacke et al. | |
| 2012/0301004 A1* | 11/2012 | Kingston | A61B 6/032 |
| | | | 382/131 |
| 2012/0314926 A1 | 12/2012 | Ghosh et al. | |
| 2013/0113486 A1 | 5/2013 | Imamura et al. | |
| 2013/0249554 A1 | 9/2013 | Simonetti et al. | |
| 2013/0265046 A1* | 10/2013 | Koch | G01R 33/56536 |
| | | | 324/309 |
| 2013/0281822 A1* | 10/2013 | Graziani | A61B 5/055 |
| | | | 600/410 |
| 2014/0002080 A1* | 1/2014 | Den Harder | G01R 33/445 |
| | | | 324/309 |
| 2014/0212012 A1* | 7/2014 | Fain | G01R 33/5601 |
| | | | 382/131 |
| 2014/0212015 A1 | 7/2014 | Ding et al. | |
| 2015/0293198 A1* | 10/2015 | Grodzki | A61B 5/055 |
| | | | 324/309 |
| 2016/0306021 A1* | 10/2016 | Weber | A61N 1/403 |

\* cited by examiner

SYSTEMS AND METHODS FOR CALIBRATED MULTI-SPECTRAL MAGNETIC RESONANCE IMAGING

CROSS-REFERENCE TO RELATED APPLICATIONS

This application represents the national stage entry of PCT International Application No. PCT/US2016/032383 filed on May 13, 2016, which claims the benefit of U.S. Provisional Patent Application Ser. No. 62/162,001 filed on May 15, 2015, and entitled "SYSTEMS AND METHODS FOR CALIBRATED THREE-DIMENSIONAL MULTI-SPECTRAL MAGNETIC RESONANCE IMAGING," both of which are herein incorporated by reference in their entirety.

BACKGROUND OF THE INVENTION

The field of the invention is systems and methods for magnetic resonance imaging ("MRI"). More particularly, the invention relates to systems and methods for MRI near metallic implants or devices.

MRI soft-tissue contrast can add substantial diagnostic value when assessing the tissue envelope around metallic implants. For example, the U.S. Food and Drug Association ("FDA") issued a recommendation for using MRI in imaging assessments of recently recalled total hip replacements. Despite this inherent utility, magnetic susceptibility artifacts generated by implants have historically limited MRI's practical clinical application in assessments of instrumented joints. In response to this clinical need, Three-Dimensional Multi-Spectral Imaging ("3D-MSI") technology was developed by the MRI research community to reduce susceptibility artifacts due to implanted devices.

One 3D-MSI technology is known as MAVRIC (Multi-Acquisition Variable-Resonance Image Combination). MAVRIC uses 3D fast spin echo ("FSE") pulse sequences specifically designed to minimize metallic artifacts around metallic prostheses.

In order to the address the substantial magnetic susceptibilities of large metallic implants such as hip implants, MAVRIC and other 3D-MSI techniques are designed to address "worst-case-scenario" imaging problems. These techniques acquire sections around the metal implant at discrete Larmor frequency offsets that account for the field perturbations. The sections are then combined to generate an image of the tissue surrounding the metal implant. Typically, such techniques may use at least twenty different sections, referred to as "spectral bins" or "frequency bins" to create a single image. Capturing these bins can sometimes take as long as ten minutes. A patient must remain still during the duration of the acquisition, which, as the acquisition becomes longer, can lead to blurred images resulting from patient movement.

There remains a need for a 3D-MSI technique that requires less scan time and, thus, reduces the risk for image blurring from subject motion. Such a method would also have the benefit of increased patient comfort because of the reduced duration of time the patient is required to be in the MRI scanner.

SUMMARY OF THE INVENTION

The present invention overcomes the aforementioned drawbacks by providing systems and methods for improved three-dimensional multi-spectral imaging ("MSI") using magnetic resonance imaging ("MRI"). In general, the 3D-MSI acquisition is improved using a calibration "pre-scan" where information from the calibration scan can be used to optimize the scanning and data collection of the 3D-MSI acquisition.

It is an aspect of the invention to provide a computer-implemented method for determining magnetic resonance imaging ("MRI") scan parameters for a three-dimensional multi-spectral imaging ("MSI") scan. The method includes providing to a computer system, calibration data acquired with an MRI system from a subject in which a metallic object is present. A field map is calculated from the calibration data. This field maps contains information about off-resonance effects caused by the metallic object. A spectral range is determined from the computed field map, and a number of spectral bins based on the determined spectral range is set. Scan parameters are then generated based on the number of spectral bins and the determined spectral range. The scan parameters define the spectral bins at which data are to be acquired with an MRI system performing a three-dimensional MSI scan.

It is another aspect of the invention to provide a method for producing an image of a subject in which a metallic object is present using an MRI system. Calibration data are acquired from the subject using the MRI system, and a spectral range is determined from the acquired calibration data. A number of spectral bins based on the determined spectral range is then set, and data are acquired from the subject using the MRI system. These data are acquired at the number of spectral bins in the spectral range. An image of the subject is then reconstructed from the acquired data, where one image is reconstructed for each spectral bin. A desired image of the subject is then produced by combining these reconstructed images.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for Interpreting the scope of the invention.

BRIEF DESCRIPTION OF THE DRAWINGS

FIG. 1 is a flowchart setting forth the steps of an example method for

DETAILED DESCRIPTION OF THE INVENTION

Described here are systems and methods for performing a calibration "pre-scan" prior to acquiring data using a multi-spectral imaging ("MSI") acquisition, such that information from the calibration scan can be used to optimize the scanning and data collection during the remainder of the MSI scan. As a result, scan times and motion artifacts are reduced. In addition, image resolution can be increased, thereby improving image quality. As one example, the MSI acquisition can be a MAVRIC acquisition. The methods described here are advantageous not only for 3D-MSI acquisitions, but also for 2D-MSI acquisitions and, thus, can be implemented for both 2D and 3D acquisitions.

In general, the calibration scan acquires information about the range and location of off-resonant spins, and can aid in optimizing the efficiency of MRI scanning when metallic implants are a factor. For example, the calibration data contains data acquired at a number of different resonance frequency offsets. The calibration data acquired with this Initial "pre-scan," or calibration scan, can be used to automatically determine off-resonance frequency ranges. As one example, the method rapidly collects a 3D-MSI dataset and then analyzes the spectral information of that data in order to guide the MR acquisitions for the rest of the 3D-MSI scan. As a result, the number of spectral bins can be reduced, with a consequent reduction in scan time, without loss in image quality. For example, the number of spectral bins can be reduced from 24 bins to as few as 3-5 bins.

The systems and method described here provide additional benefits, including artifact reduction and workflow improvement. For instance, low-artifact imaging can be improved near indwelling metallic implants or other metallic devices. Workflow can also be improved because current metal artifact reduction technologies are "blind" to the type of implant presented, but there can be a significant difference between the artifacts generated by different implants. Currently, imaging sequences are designed for a worst-case scenario and perform the maximum amount of artifact correction. With the methods described here, however, the 3D-MSI scan can be tailored to the particular implant (e.g., by using the minimum number of spectral bins for a particular Implant), thereby increasing efficiency of the scan.

As an example, many existing 3D-MSI techniques are hard-coded for a worst-case scenario, such as the metallic implant or device being composed of stainless steel or cobalt-chromium. In many Instances, however, implants and devices are composed of other materials that require less artifact reduction. The systems and methods described here can guide what type of, and how much, artifact correction to provide.

Figure 1:
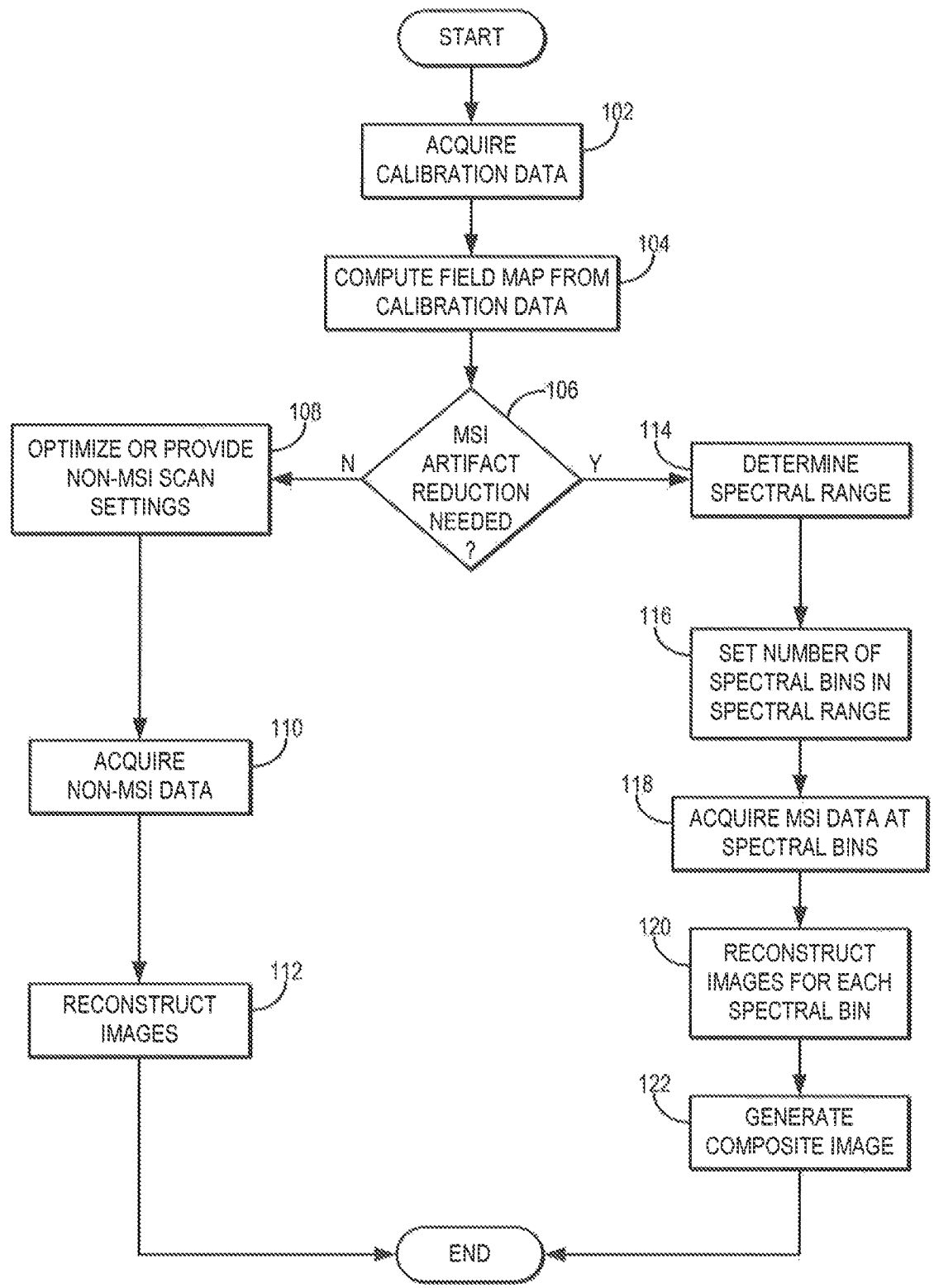

Referring now to FIG. 1, a flowchart is illustrated as setting forth the steps of an example method for calibrating a 3D-MSI acquisition. In general, the method includes collecting a calibration dataset and then analyzing the spectral information in that calibration dataset to guide the remainder of the 3D-MSI acquisition.

The method thus includes acquiring calibration data, as Indicated at step 102. In general, the calibration data can be acquired as a low-resolution, non-selective 3D-MSI dataset. As one example, the calibration data can be acquired using a rapid MAVRIC acquisition. As another example, the calibration data can be acquired using a selective MAVRIC acquisition, such as a MAVRIC SL acquisition. When using MAVRIC SL, or similar selective acquisition techniques, a linear $B_0$ trend can be removed in the slab-selective dimension before additional processing is performed. In some examples, the calibration data can also be acquired using a two-dimensional acquisition when a 2D-MSI scan is planned.

Based on the calibration data, a field map, or off-resonance map, is computed, as indicated at step 104. The field map contains information about off-resonance effects in the field-of-view imaged by the calibration data. As one example, these off-resonance effects can be caused by metallic objects, such as implants or devices, that may be present in the subject being Imaged. Calibration images can also be reconstructed from the calibration data at this point.

A determination is then made at decision block 106 whether 3D-MSI artifact reduction is needed based on the type of metallic implant or device present in the subject. This determination can be based, at least in part, on analysis of the field map. As an example, if there is not a significant amount of resonance frequency offset in the field map, then it may be determined that artifact reduction is not necessary.

If it is determined that artifact reduction is unnecessary, then the method proceeds by computing or otherwise providing the optimal settings (e.g., receiver bandwidth, number of averages) for a non-3D-MSI acquisition, as indicated at step 108. Non-3D-MSI data is then acquired from the subject, as indicated at step 110, from which images of the subject can be reconstructed, as indicated at step 112.

If, however, analysis of the field map determines that artifact reduction using 3D-MSI techniques is necessary, or otherwise desirable, then the method proceeds by determining the spectral range to be used for a 3D-MSI acquisition, as indicated at step 114. This spectral range is determined based on the field map generated from the calibration data.

Figure 2:
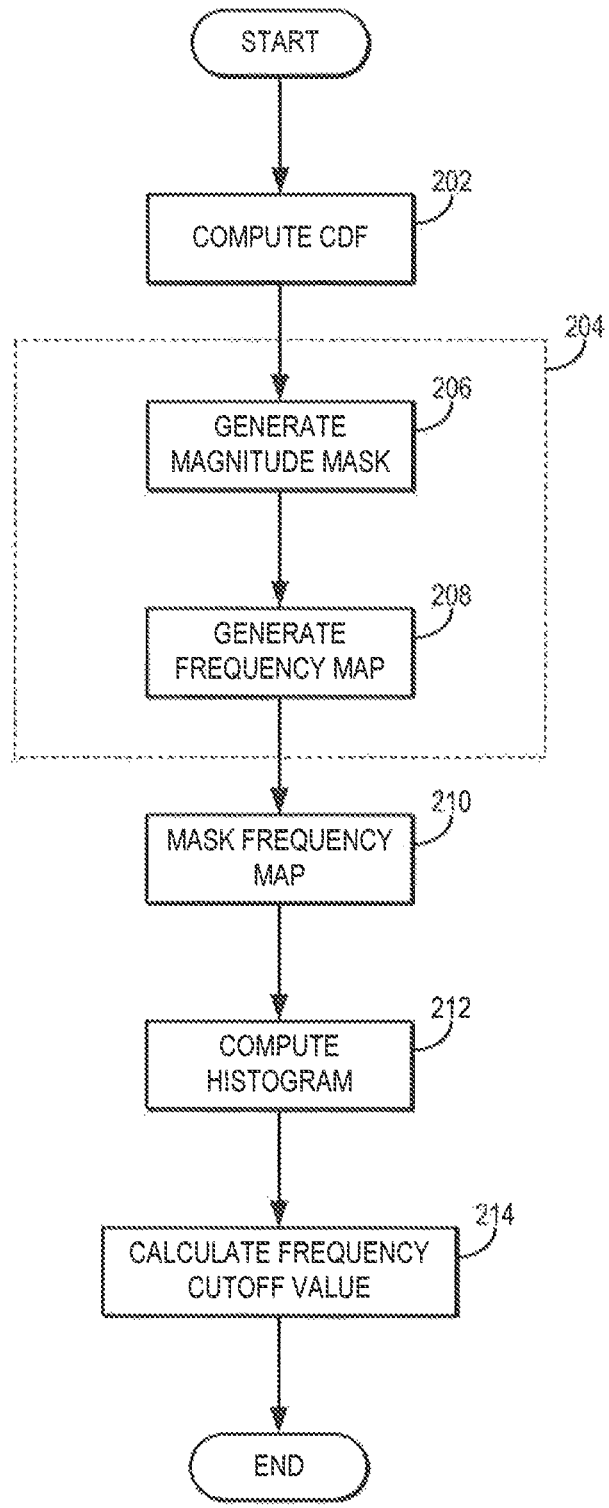
FIG. 2 is a flowchart setting forth the steps of an example method for determining a spectral range based on a cumulative distribution function computed from a field map.

As one example, the spectral range can be determined based on a cumulative distribution function ("CDF") computed from the field map. Referring now to FIG. 2, a flowchart is illustrated at setting forth the steps of an example method for determining a spectral range based on a CDF that is computed from the field map. This method begins by computing a CDF from the estimated field map, as indicated at step 202. In general, the CDF can be computed by estimating a probability density function ("PDF") from the field map, and then computing the integral of the PDF. As one example, the PDF can be estimated as the histogram of the distribution of frequencies in the field map.

As generally indicated at process block 204, magnitude and frequency map masks are generated and used in the process of determining the spectral range. First, a magnitude mask is generated, as indicated at step 206. Then, using the magnitude mask, a frequency map is generated, as indicated at step 208. As one example, the magnitude mask can be computed from a high intensity mask and a low intensity mask that are generated based on the CDF and the calibration images reconstructed from the calibration data, as will be described below.

The dynamic range of magnitude images reconstructed from the calibration data is generally dominated by high intensity signal from fat tissues. In addition to the high signal intensities from the fat tissues, subtle streak artifacts can also be present in these magnitude images. These high signal intensities can be removed from the calibration images to provide for the later generated frequency map to be calculated accurately.

As one non-limiting example, the high intensity mask can be generated as follows. The intensities that retain ninety percent of the signal intensities are used to normalize the magnitude image. Signal intensities in this normalized image that are greater than or equal to one are then set to have zero values. The CDF can optionally be recomputed based on this normalized image to adjust the high intensity mask. For instance, the high intensity mask can be updated based on the recomputed CDF by setting intensities greater than ninety-nice percent to have zero values.

Extremely low signal intensities in the magnitude image lead to high frequency streaks in the later generated frequency map. Thus, to reduce biases in the frequency map, these low signal intensities can be removed from the calibration images. As one non-limiting example of creating a low intensity mask, normalized intensities that are lower than three percent can be set to zero.

Based on the high intensity and low intensity masks, the magnitude mask can be generated. For example, the magnitude mask can be created by setting all non-zero intensities in the high intensity and low intensity signal masks to one, while all other values remain zero.

Using the magnitude mask, a frequency map is generated at step 208, as mentioned above. As one example, the frequency map can be computed using the magnitude images from the individual spectral bins of the image reconstructed from the calibration data. The frequency map is then masked using the magnitude mask, as indicated at step 210. From the masked frequency map, a histogram is computed, as indicated at step 212.

A frequency cutoff that defines the spectral range is then calculated, as indicated at step 214. As one example, to account for an asymmetric histogram, a forward and backward CDF are first computed from the histogram. The forward CDF is computed by integrating from the low frequencies to the high frequencies, and the backward CDF is computed by integrating from the high frequencies to the low frequencies. A frequency cutoff is then computed for each of the forward and backward CDF. As one example, the frequency cutoff can be selected as the cutoff value that retains ninety-nine percent of the frequencies in the map. The frequency cutoff value that has the larger absolute value can be chosen as the final frequency cutoff value. In most instances, the final frequency cutoff value retains the sign of the selected cutoff value and the absolute value is just used as a check to select the final frequency cutoff value. As will be described below in more detail, frequency cutoff values can then be used to compute the number (e.g., the minimum number) of spectral bins to be used for a 3D-MSI acquisition.

Figure 3:
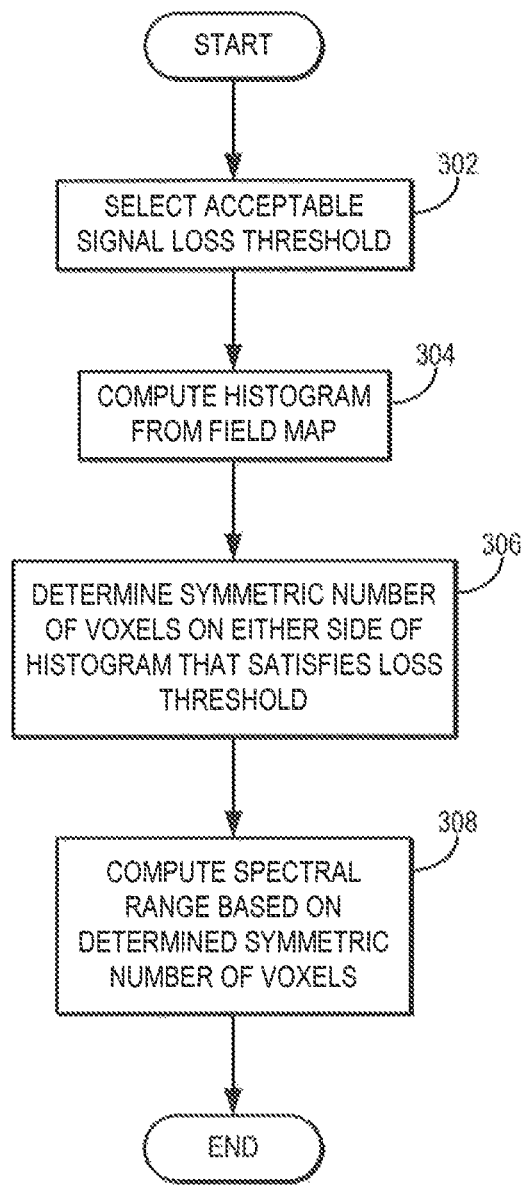
FIG. 3 is a flowchart setting forth the steps of an example method for determining a spectral range based on residual signal volume beyond a spectral cutoff.

Referring now to FIG. 3, as another example, the spectral range can be determined by computing the residual signal volume beyond a spectral cutoff. FIG. 3 illustrates a flowchart setting forth the steps of an example method of such an approach for determining the spectral range.

In this method, an acceptable signal loss threshold is first selected, as indicated at step 302. This acceptable signal loss threshold value describes an acceptable level of missing volumetric tolerance around the metallic implant or device interface. A histogram is then computed from the estimated field map, as indicated at step 304.

A symmetric number of voxels on either side of the histogram distribution summing to the volumetric tolerance defined by the selected signal loss threshold is then determined, as indicated at step 306. The range of frequencies between the frequency bin values for these two histogram bins is then computed and used to determine the spectral range, as indicated at step 308. These two frequency bin values define a cutoff frequency that demarcates the spectral range that can be used for 3D-MSI acquisitions.

It should be appreciated that additional methods for determining the desired spectral range beyond the two methods described above can also be implemented. For example, the signal energy or power in each spectral bin could be analyzed and used to determine the spectral range. When the energy or power drops below a pre-defined threshold in a given spectral bin, the limits on that bin can also be determined.

Referring again to FIG. 1, after the spectral range is determined, the number of spectral bins in the spectral range is set, as indicated at step 116. The spectral bins are associated with the frequencies at which spins are to be excited (i.e., the frequencies at which RF is transmitted) and at which data are to be collected (i.e., the frequencies at which the RF receiver will detect signals). As one example, the number of spectral bins can be calculated as, $$\text{round}(2 \cdot f_{cutoff}+1) \quad (1);$$

where $f_{cutoff}$ is the frequency cutoff defined by the determined spectral range. 3D-MSI data is then acquired at the selected spectral bins, as indicated at step 118. As one example, the 3D-MSI data are acquired using a MAVRIC acquisition technique. From the 3D-MSI data, images for each spectral bin are reconstructed, as indicated at step 120, and a composite image can be generated by combining the 3D-MSI images for each spectral bin, as indicated at step 122.

Optionally, before the 3D-MSI data are acquired, a determination can be made whether spatial saturation pulses can be used for imaging the metallic implant or device. In this configuration, a user interface can be updated to depict regions of valid saturation pulse placement.

A 3D-MSI calibration scan has thus be described. These 3D-resolved MSI calibration images have a number of potential uses. For instance, through adaptive modulation of the acquired spectral bins, substantial acquisition efficiency can be gained in MAVRIC, MAVRIC SL, or other 3D-MSI scans where fewer bins are needed. This time savings can be substantial for smaller implants or for implants made of lower susceptibility metals such as titanium screws or oxidized zirconium joint replacements.

In general, the accuracy of the off-resonance range distribution determination is limited by the resolution of the calibration maps; however, it is contemplated that this spatial inaccuracy will not have significant impact on computing the numbers of spectral bins that contain clinically relevant amounts of signal.

Although reference is made to MAVRIC acquisitions above, the calibration scheme described here is also applicable for other 3D-MSI techniques, including the SEMAC technique. For example, the calibrated spatial off-resonance distribution could be utilized to optimize the number of slice encodes applied to each slice. In addition, the off-resonance distribution can be used to inform hexagonal sampling SEMAC methods.

Figure 4:
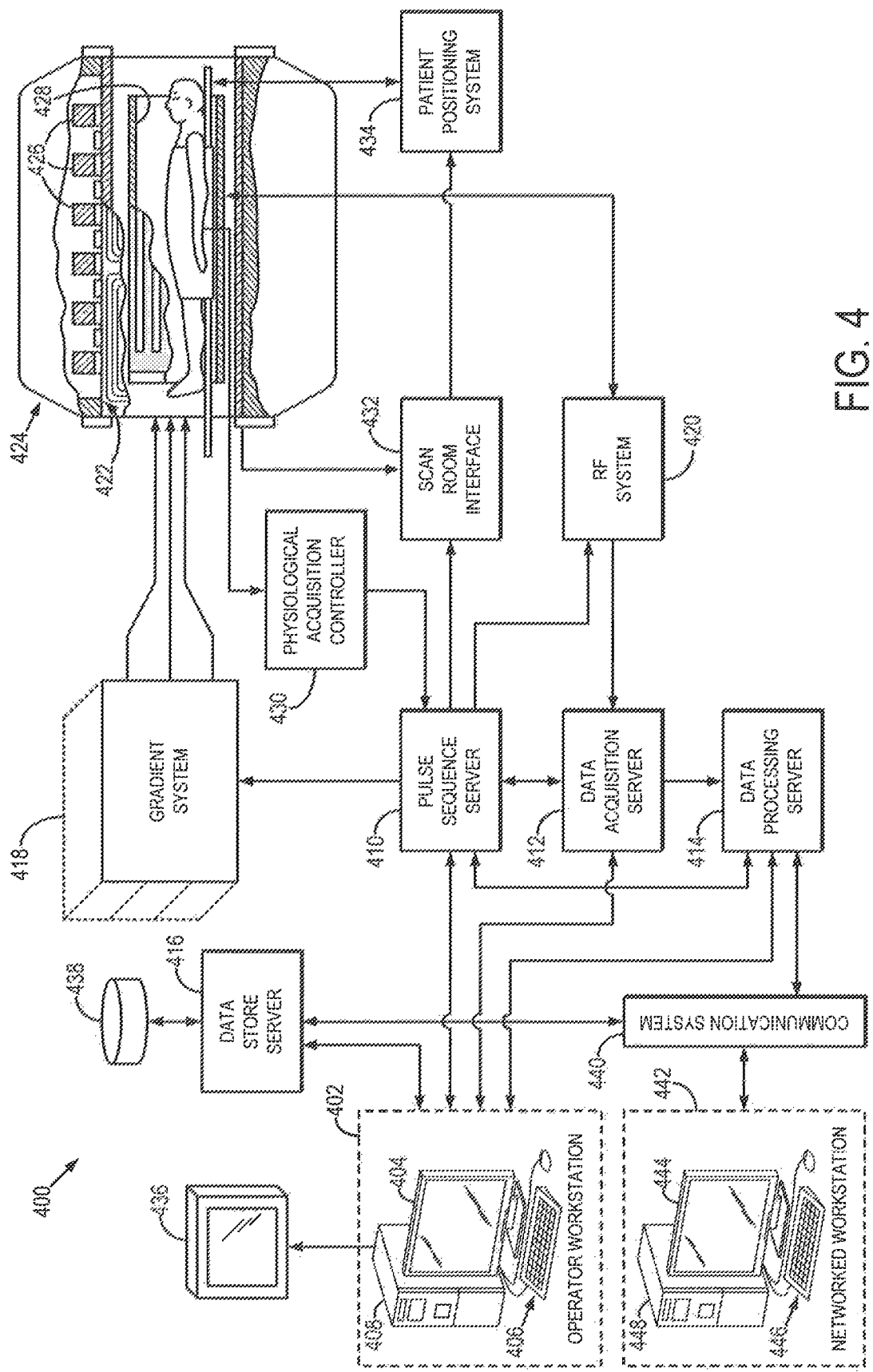
FIG. 4 is a block diagram of an example of a magnetic resonance imaging ("MRI") system.

Referring particularly now to FIG. 4, an example of a magnetic resonance imaging ("MRI") system 400 that can implement the methods described here is illustrated. The MRI system 400 includes an operator workstation 402 that may include a display 404, one or more input devices 406 (e.g., a keyboard, a mouse), and a processor 408. The processor 408 may include a commercially available programmable machine running a commercially available operating system. The operator workstation 402 provides an operator interface that facilitates entering scan parameters into the MRI system 400. The operator workstation 402 may be coupled to different servers, including, for example, a pulse sequence server 410, a data acquisition server 412, a data processing server 414, and a data store server 416. The operator workstation 402 and the servers 410, 412, 414, and 416 may be connected via a communication system 440, which may include wired or wireless network connections.

The pulse sequence server 410 functions in response to instructions provided by the operator workstation 402 to operate a gradient system 418 and a radiofrequency ("RF") system 420. Gradient waveforms for performing a prescribed scan are produced and applied to the gradient system 418, which then excites gradient coils in a gradient coil assembly 422 to produce the magnetic field gradients $G_x$, $G_y$, and $G_z$ that are used for spatially encoding magnetic resonance signals. The gradient coil assembly 422 forms part of a magnet assembly 424 that includes a polarizing magnet 426 and a whole-body RF coil 428.

RF waveforms are applied by the RF system 420 to the RF coil 428, or a separate local coil to perform the prescribed magnetic resonance pulse sequence. Responsive magnetic resonance signals detected by the RF coil 428, or a separate local coil, are received by the RF system 420. The responsive magnetic resonance signals may be amplified, demodulated, filtered, and digitized under direction of commands produced by the pulse sequence server 410. The RF system 420 includes an RF transmitter for producing a wide variety of RF pulses used in MRI pulse sequences. The RF transmitter is responsive to the prescribed scan and direction from the pulse sequence server 410 to produce RF pulses of the desired frequency, phase, and pulse amplitude waveform. The generated RF pulses may be applied to the whole-body RF coil 428 or to one or more local coils or coil arrays.

The RF system 420 also includes one or more RF receiver channels. An RF receiver channel includes an RF preamplifier that amplifies the magnetic resonance signal received by the coil 428 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \quad (2);$$

and the phase of the received magnetic resonance signal may also be determined according to the following relationship:

$$\varphi = \tan^{-1}\left(\frac{Q}{I}\right). \quad (3)$$

The pulse sequence server 410 may receive patient data from a physiological acquisition controller 430. By way of example, the physiological acquisition controller 430 may receive signals from a number of different sensors connected to the patient, including electrocardiograph ("ECG") signals from electrodes, or respiratory signals from a respiratory bellows or other respiratory monitoring devices. These signals may be used by the pulse sequence server 410 to synchronize, or "gate," the performance of the scan with the subject's heart beat or respiration.

The pulse sequence server 410 may also connect to a scan room interface circuit 432 that receives signals from various sensors associated with the condition of the patient and the magnet system. Through the scan room interface circuit 432, a patient positioning system 434 can receive commands to move the patient to desired positions during the scan.

The digitized magnetic resonance signal samples produced by the RF system 420 are received by the data acquisition server 412. The data acquisition server 412 operates in response to instructions downloaded from the operator workstation 402 to receive the real-time magnetic resonance data and provide buffer storage, so that data Is not lost by data overrun. In some scans, the data acquisition server 412 passes the acquired magnetic resonance data to the data processing server 414. In scans that require information derived from acquired magnetic resonance data to control the further performance of the scan, the data acquisition server 412 may be programmed to produce such information and convey it to the pulse sequence server 410. For example, during pre-scans, magnetic resonance data may be acquired and used to calibrate the pulse sequence performed by the pulse sequence server 410. As another example, navigator signals may be acquired and used to adjust the operating parameters of the RF system 420 or the gradient system 418, or to control the view order in which k-space is sampled. In still another example, the data acquisition server 412 may also process magnetic resonance signals used to detect the arrival of a contrast agent in a magnetic resonance angiography ("MRA") scan. For example, the data acquisition server 412 may acquire magnetic resonance data and processes it in real-time to produce information that is used to control the scan.

The data processing server 414 receives magnetic resonance data from the data acquisition server 412 and processes the magnetic resonance data in accordance with instructions provided by the operator workstation 402. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 414 are conveyed back to the operator workstation 402 for storage. Real-time images may be stored in a data base memory cache, from which they may be output to operator display 402 or a display 436. Batch mode images or selected real time images may be stored in a host database on disc storage 438. When such images have been reconstructed and transferred to storage, the data processing server 414 may notify the data store server 416 on the operator workstation 402. The operator workstation 402 may be used by an operator to archive the images, produce films, or send the images via a network to other facilities.

The MRI system 400 may also include one or more networked workstations 442. For example, a networked workstation 442 may include a display 444, one or more input devices 446 (e.g., a keyboard, a mouse), and a processor 448. The networked workstation 442 may be located within the same facility as the operator workstation 402, or in a different facility, such as a different healthcare institution or clinic.

The networked workstation 442 may gain remote access to the data processing server 414 or data store server 416 via the communication system 440. Accordingly, multiple networked workstations 442 may have access to the data processing server 414 and the data store server 416. In this manner, magnetic resonance data, reconstructed images, or other data may be exchanged between the data processing server 414 or the data store server 416 and the networked workstations 442, such that the data or images may be remotely processed by a networked workstation 442.

The present invention has been described in terms of one or more preferred embodiments, and it should be appreciated that many equivalents, alternatives, variations, and modifications, aside from those expressly stated, are possible and within the scope of the invention.

The invention claimed is:

1. A computer-implemented method for determining magnetic resonance imaging ("MRI") scan parameters for a multi-spectral imaging ("MSI") scan, the steps of the method comprising:

(a) providing to a computer system, calibration data acquired with an MRI system from a field-of-view, wherein the calibration data contains data acquired at a plurality of different resonance frequency offsets;

(b) computing with the computer system, a field map from the calibration data, the field map containing information about off-resonance effects in the field-of-view;

(c) determining with the computer system, a spectral range from the computed field map;

(d) setting with the computer system, a number of spectral bins based on the determined spectral range;

(e) generating with the computer system, scan parameters based on the number of spectral bins and the determined spectral range, the scan parameters defining the spectral bins at which spins are to be excited and data are to be acquired with an MRI system performing an MSI scan; and (f) sending the scan parameters to the MRI system and performing the MSI scan in order to acquire data from a subject by operating the MRI system using the scan parameters, the data being acquired at the number of spectral bins set by the computer system.

2. The method as recited in claim 1, wherein step (a) includes acquiring the calibration data with the MRI system.

3. The method as recited in claim 1, wherein the calibration data provided in step (a) have a lower spatial resolution than the data to be acquired with the MRI system using the scan parameters generated in step (e).

4. The method as recited in claim 1, wherein step (c) includes calculating with the computer system, a frequency cutoff value from a frequency map generated by the computer system from the provided calibration data.

5. The method as recited in claim 4, wherein the computer system calculates the frequency cutoff value by:
computing a histogram from the frequency map;
calculating a forward cumulative distribution function (CDF) by integrating the histogram from low frequencies to high frequencies;
calculating a backward CDF by integrating the histogram from high frequencies to low frequencies;
determining a first frequency cutoff value using the forward CDF to identify a frequency value that retains a selected amount of signal intensities in the frequency map;
determining a second frequency cutoff value using the backward CDF to identify a frequency value that retains the selected amount of signal intensities in the frequency map; and
selecting the frequency cutoff value based on a value of the first frequency cutoff value and a value of the second frequency cutoff value.

6. The method as recited in claim 5, wherein the frequency cutoff value is selected as a signed value of the one of the first frequency cutoff value and second frequency cutoff value having a greater absolute value.

7. The method as recited in claim 4, wherein the computer system computes a magnitude mask from the calibration data and masks the frequency map with the magnitude mask before calculating the frequency cutoff value.

8. The method as recited in claim 7, wherein the magnitude mask includes a high-intensity mask that masks high signal intensities and a low-intensity mask that masks low signal intensities.

9. The method as recited in claim 4, wherein the computer system generates the frequency map from magnitude images reconstructed from the calibration data.

10. The method as recited in claim 4, wherein step (d) includes setting the number of spectral bins as an integer closest to, wherein is the frequency cutoff value.

11. The method as recited in claim 1, wherein step (c) includes calculating with the computer system, a frequency cutoff value based on a signal loss threshold that defines an acceptable level of signal loss in a volume around the metallic object.

12. The method as recited in claim 11, wherein the computer system calculates the frequency cutoff by:
computing a histogram from the field map;
determining a symmetric number of voxels on either side of the histogram that sum to a volumetric tolerance defined by the signal loss threshold; and
computing the frequency cutoff value based on the determined symmetric number of voxels.

13. The method as recited in claim 12, wherein step (d) includes setting the number of spectral bins as an integer closest to, wherein is the frequency cutoff value.

14. The method as recited in claim 1, wherein the off-resonance effects in the field-of-view are caused by a metallic object in the field-of-view, and wherein the metallic object is at least one of a metallic implant or a metallic device.

15. The method as recited in claim 1, wherein the calibration data are three-dimensional calibration data.

16. The method as recited in claim 15, wherein the MSI scan is a three-dimensional MSI scan.

17. The method as recited in claim 1, wherein the calibration data are two-dimensional calibration data.

18. The method as recited in claim 17, wherein the MSI scan is a two-dimensional MSI scan.

19. A method for producing an image of a subject using a magnetic resonance imaging (MRI) system, the steps of the method comprising:

(a) acquiring calibration data from the subject using the MRI system, wherein the calibration data include data acquired at a plurality of different resonance frequency offsets;

(b) determining with the computer system, a spectral range from the acquired calibration data;

(c) setting with the computer system, a number of spectral bins based on the determined spectral range;

(d) acquiring data from the subject using the MRI system, the data being acquired at the number of spectral bins set by the computer system;

(e) reconstructing with the computer system, an image of the subject for each spectral bin from the acquired data; and (f) producing with the computer system, a desired image of the subject by combining the images reconstructed in step (e).

20. The method as recited in claim 19, wherein the calibration data acquired in step (a) have a lower spatial resolution than the data acquired in step (d).

21. The method as recited in claim 20, wherein step (b) includes calculating with the computer system, a frequency cutoff value from the acquired calibration data.

22. The method as recited in claim 21, wherein the computer system calculates the frequency cutoff value by:
producing a frequency map from the acquired calibration data;
computing a histogram from the frequency map;
calculating a forward cumulative distribution function (CDF) by integrating the histogram from low frequencies to high frequencies;

calculating a backward CDF by integrating the histogram from high frequencies to low frequencies;

determining a first frequency cutoff value using the forward CDF to identify a frequency value that retains a selected amount of signal intensities in the frequency map;

determining a second frequency cutoff value using the backward CDF to identify a frequency value that retains the selected amount of signal intensities in the frequency map; and selecting the frequency cutoff value based on a value of the first and second frequency cutoff values.

23. The method as recited in claim 22, wherein step (d) includes setting the number of spectral bins as an integer closest to, wherein is the frequency cutoff value.

24. The method as recited in claim 21, wherein the computer system calculates the frequency cutoff by:

selecting a signal loss threshold that defines an acceptable level of signal loss in a volume around the metallic object;

producing a field map from the calibration data;

computing a histogram from the field map;

determining a symmetric number of voxels on either side of the histogram that sum to a volumetric tolerance defined by the signal loss threshold; and computing the frequency cutoff value based on the determined symmetric number of voxels.

25. The method as recited in claim 21, wherein the computer system calculates the frequency cutoff by:

defining a threshold for an amount of volumetric imaging signal in a useable spectral bin;

finding a minimum and a maximum frequency offset spectral bin that each contain the amount of volumetric imaging signal; and computing the frequency cutoff value based on the frequency offsets of the minimum and maximum bins.

26. The method as recited in claim 19, wherein the calibration data acquired from the subject are three-dimensional calibration data.

27. The method as recited in claim 26, wherein the data acquired from the subject are three-dimensional data.

28. The method as recited in claim 19, wherein the calibration data acquired from the subject are two-dimensional calibration data.

29. The method as recited in claim 28, wherein the data acquired from the subject are two-dimensional data.

* * * * *